(12) United States Patent
Wirsing et al.

(10) Patent No.: US 9,998,072 B2
(45) Date of Patent: Jun. 12, 2018

(54) APPARATUS AND METHOD FOR LOCATING A DISCONTINUITY IN A SOLAR ARRAY

(71) Applicant: DOW GLOBAL TECHNOLOGIES LLC, Midland, MI (US)

(72) Inventors: Douglas J. Wirsing, Midland, MI (US); Michael J. Lesniak, Kawkawlin, MI (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 729 days.

(21) Appl. No.: 14/398,164

(22) PCT Filed: Apr. 12, 2013

(86) PCT No.: PCT/US2013/036268
§ 371 (c)(1),
(2) Date: Oct. 31, 2014

(87) PCT Pub. No.: WO2013/188000
PCT Pub. Date: Dec. 19, 2013

(65) Prior Publication Data
US 2015/0107642 A1   Apr. 23, 2015

Related U.S. Application Data

(60) Provisional application No. 61/658,571, filed on Jun. 12, 2012.

(51) Int. Cl.
*G01R 31/02* (2006.01)
*H02S 50/10* (2014.01)
(Continued)

(52) U.S. Cl.
CPC ............ *H02S 50/10* (2014.12); *A01N 1/0221* (2013.01); *H01L 31/0201* (2013.01)

(58) Field of Classification Search
None
See application file for complete search history.

(56) References Cited

U.S. PATENT DOCUMENTS 3,696,286 A    10/1972  Ule
4,301,409 A *  11/1981  Miller ................... H02S 50/10
                                                    136/290
(Continued)

FOREIGN PATENT DOCUMENTS

DE   102006028056 A1   12/2007
DE   102010036514 A1    1/2012
(Continued)

OTHER PUBLICATIONS

Partial translation of Prior et al. (EP 2388603 A1).*
(Continued)

*Primary Examiner* — Magali P Slawski

(57) ABSTRACT

A kit comprising one or more of the following one or more solar modules (10); one of more connectors (30); and one or more integrated flashing pieces (40), wherein the one or more solar modules, the one or more connectors, and the one or more integrated flashing pieces include a first buss (16) and a second buss (18); wherein the one or more solar modules, the one or more connectors, the one or more integrated flashing pieces, or a combination thereof include a capacitor between the first buss and the second buss so that the capacitor blocks direct current from passing through the first buss, the second buss, or both and allows an alternating: current signal, an alternating voltage signal or both to pass trough the first buss, the second buss, or both so that a discontinuity, partial discontinuity, or continuity of the one more solar modules, the one or more, connectors, the one or more integrated flashing pieces, or a combination of connections therebetween are detectable when the one or more (Continued)

solar modules, the one or more connectors, and the one or more integrated flashing pieces are electrically connected.

20 Claims, 4 Drawing Sheets

(51) Int. Cl.
*A01N 1/02* (2006.01)
*H01L 31/02* (2006.01)

(56) References Cited

U.S. PATENT DOCUMENTS

| | | | |
|---|---|---|---|
| 4,676,761 A | 6/1987 | Poujois | |
| 4,695,788 A | 9/1987 | Marshall | |
| 6,979,771 B2 | 12/2005 | Mimura | |
| 8,039,783 B2 | 10/2011 | Lai | |
| 2003/0059966 A1 | 3/2003 | Ellison | |
| 2003/0153145 A1* | 8/2003 | Sandhu | H01L 27/10852 438/239 |
| 2005/0135129 A1* | 6/2005 | Kazutoshi | H02J 5/005 363/98 |
| 2010/0236035 A1 | 9/2010 | Chung | |

FOREIGN PATENT DOCUMENTS

| | | | | |
|---|---|---|---|---|
| EP | 1918727 A1 | 5/2008 | | |
| EP | 2388603 A1 * | 11/2011 | ........... | G01R 31/026 |
| GB | 2463556 A | 3/2010 | | |
| JP | S-A-5920870 | 2/1984 | | |
| WO | 87/07731 A1 | 12/1987 | | |
| WO | 97/14047 A1 | 4/1997 | | |
| WO | 98/32024 A1 | 7/1998 | | |
| WO | 2006/076893 A1 | 7/2006 | | |
| WO | 2007/076846 A1 | 7/2007 | | |
| WO | 2011/017772 A1 | 2/2011 | | |
| WO | 2011/1511672 A1 | 12/2011 | | |
| WO | 2012/000533 A1 | 1/2012 | | |

OTHER PUBLICATIONS

International Search Report and Written Opinion, Application No. PCT/US2013/036268 dated Jul. 15, 2013.
Progressive Electronic 200EP Induction Amplifier available at: http://www.amazon.com/Progressive-Electronic-Inductive-Amplifier-Tracer/dp/B007M2BZJY, dated Apr. 3, 2012.
International Preliminary Examining Authority, Application No. PCT/US2013/036268 dated Jun. 17, 2014.
International Preliminary Report on Patentability, Application No. PCT/US2013/036268 dated Sep. 23, 2014.

* cited by examiner

APPARATUS AND METHOD FOR LOCATING A DISCONTINUITY IN A SOLAR ARRAY

FIELD

The present teachings relate to an apparatus and method for detecting open circuits (i.e., discontinuities) at a location along a solar array.

BACKGROUND

The present teachings are predicated upon providing an improved apparatus and method for detecting discontinuities and/or partial discontinuities in a solar array. Each solar array is comprised of a combination of solar modules, connection devices, and integrated flashing pieces. Once all of the pieces are combined together a solar array is formed and power is passed from the solar array to an inverter so that the power may be used. Generally, each solar module, connection device, and integrated flashing piece includes a buss bar adding to the points of contact in the solar array. Depending upon the number of solar modules a solar array can have as many as 600 connection points or more. If these connections fail, power from the solar array to the inverter is reduced and/or eliminated. When this condition occurs it can be difficult to isolate the exact location of the cause of the reduction and/or elimination of power from the solar array to the inverter. Adding to the difficulty in detecting the exact location of the discontinuity, the solar array may be located in a loud environment such as next to an airport or a factory; in hard to reach locations such as roof tops; or the like.

Devices and methods to detect the discontinuities exist; however, some of these devices may be too large and/or expensive to use in an "on-site" location such as a roof top. Haste and/or loss of attention by the user, surrounding environmental conditions, or both may lead to inaccurate readings and/or multiple attempts to locate a discontinuity and/or partial discontinuity. Further, some of these devices have difficulty in detecting partial discontinuities. Other devices may not pinpoint the connection causing the discontinuity, thus, increasing the time and complexity in repairing the solar array. Examples of devices and/or methods used to locate discontinuities in a solar array may be found in U.S. Pat. Nos. 3,696,286; 4,695,788; and 6,979,771; U.S. Patent Application Publication Nos. 2003/0059966 and 2010/0236035; International Patent Nos. WO87/07731; WO97/14047; WO98/32024; WO2006/076893; WO2007/076846; and Progressive Electronic 200EP Induction Amplifier available at: http://www.amazon.com/Prooressive-Electronic-Inductive-Amplifier-Tracer/dp/B007M2BZJY, all of which are incorporated by reference herein for all purposes.

It would be attractive to have a device and/or method that provides an output regarding whether the tested locations are continuous, discontinuous, or partially discontinuous. It would be attractive to have an apparatus that assists in isolating a signal so that a status of a connection is accurately determined. What is needed is a detection device that enables a user to accurately locate a discontinuity and/or partial discontinuity in a long buss. What is further needed is a device and method of isolating signal so that the signal may be used to locate discontinuities and/or partial discontinuities in a solar array.

SUMMARY

The present teachings provide: a kit comprising one or more of the following: one or more solar modules; one or more connectors; and one or more integrated flashing pieces wherein the one or more solar modules, the one or more connectors, and the one or more integrated flashing pieces include a first buss and a second buss; wherein the one or more solar modules, the one or more connectors, the one or more integrated flashing pieces, or a combination thereof include a capacitor between the first buss and the second buss so that the capacitor blocks direct current from passing through the first buss, the second buss, or both and allows an alternating current signal, an alternating voltage signal, or both to pass through the first buss, the second buss, or both so that a discontinuity, partial discontinuity, or continuity of the one or more solar modules, the one or more connectors, the one or more integrated flashing pieces, or a combination of connections therebetween are detectable when the one or more solar modules, the one or more connectors, and the one or more integrated flashing pieces are electrically connected.

The present teachings further include: a solar array comprising: one or more solar modules; one or more connectors located between and electrically connecting the one or more solar modules; one or more integrated flashing pieces connected to one or more connectors, one or more solar modules, or both and one or more capacitors electrically connected to the one or more solar modules, the one or more connectors, one or more integrated flashing pieces, or a combination thereof; wherein the one or more solar modules, the one or more connectors and the one or more integrated flashing pieces have a first buss and a second buss and the one or more capacitors are connected to the first buss and the second buss; wherein the one or more capacitors block direct current from passing through the one or more buss structures so that a discontinuity, partial discontinuity, or both along the solar array are detected by measuring alternating current levels, an alternating voltage signal, or both as a signal stimulus is moved along the solar array.

The present teachings include a method comprising: inducing a signal by applying a signal stimulus to the solar array taught herein so that the signal stimulus produces an alternating current signal and an alternating voltage signal; measuring the alternating voltage signal, the alternating current signal, or both at one or more points along the solar array using a detector; providing feedback regarding whether the solar array has continuity, discontinuity, or a partial discontinuity based upon a measurement taken at the one or more points along the solar array.

The teachings herein surprisingly solve one or more of these problems by providing a device and/or method that provides an output regarding whether the tested locations are continuous, discontinuous, or partially discontinuous. The present teachings provide an apparatus that assists in isolating a signal so that a status of a connection is accurately determined. The teachings herein include a detection device that enables a user to accurately locate a discontinuity and/or partial discontinuity in a long buss. The teachings herein provide a device and method of isolating signal so that the signal may be used to locate discontinuities and/or partial discontinuities in a solar array.

DETAILED DESCRIPTION

Figure 1:
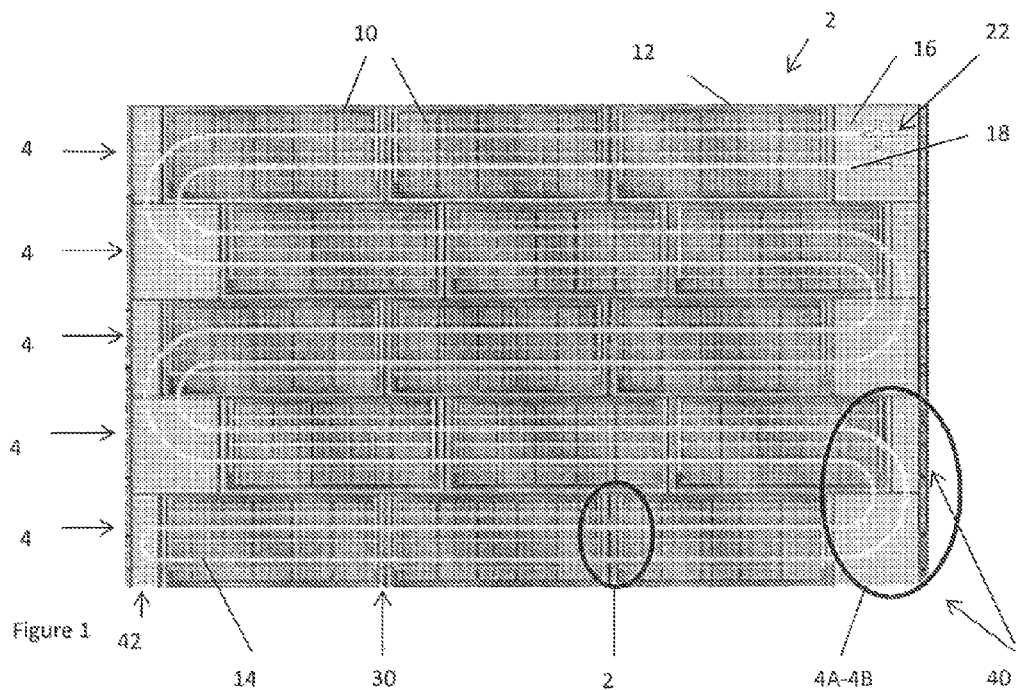
FIG. 1 illustrates one example of a solar array.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Specific embodiments of the present teachings as set forth are not intended as being exhaustive or limiting. The scope of the teachings should be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

Generally a solar array taught herein includes: one or more rows of solar modules and each row includes a plurality of solar modules connected together. Each solar module in the row has a connector on each side that physically and electrically connects a first buss and a second buss of each solar module together so that power passes though the adjoining solar modules. The solar modules located at the ends of each row are connected together by an integrated flashing piece so that two adjacent rows are electrically connected. The first solar module in the solar array is electrically connected to an inverter at a buss termination point so that the inverter can convert the current into a usable power source. The last solar module in the solar array includes an integrated flashing piece that connects the first buss and the second buss of the last solar module electrically together so that power from the first buss is returned towards the inverter through the second buss. Over time environmental conditions such as temperature variations, wind, rain, snow, debris, the like, or a combination thereof, one or more of the connections detailed above in the solar array may fail so that current and/or power at the inverter is reduced and/or eliminated. The teachings herein provide a apparatus and method to test each connection point and/or identify a proximate location of a discontinuity in the solar array so that the connection can be repaired.

The present teachings herein include a solar array that may be provided as a kit. The kit may include one or more of the following, one or more connectors, one or more solar modules, one or more integrated flashing pieces, an inverter, wiring, or a combination thereof. The improved connectors, solar modules, integrated flashing pieces, or a combination thereof as taught herein may include one or more capacitors. The capacitors may be located at any point along the solar array. The capacitors may be located within one or both ends of a solar module, within an integrated flashing piece, within a connector, or a combination thereof. Preferably, the capacitors are located within one of more of the connectors that connect the solar modules together, the solar modules to the integrated flashing pieces, or a combination thereof. More preferably, each capacitor may electrically connect a first buss and a second buss together. The capacitors used may be any capacitor that includes enough capacitance so that the direct current signal is blocked from passing through the capacitor and so that the capacitor may withstand the DC voltage between the first buss and the second buss.

The capacitors may withstand a direct current voltage of about 120 volts or more, about 200 volts or more, about 250 volts or more, about 300 volts or more, or preferably about 350 volts or more. The capacitors may withstand a direct current voltage of about 600 volts or less, preferably about 550 volts or less, or more preferably about 500 volts or less. Preferably, the capacitors are sufficiently large so that the impedance of each capacitor eliminates the direct current signal and allows the alternating current signal, the alternating voltage signal, or both to pass so that the alternating current signal, the alternating voltage signal, or both may be measured. The capacitor may be selected so that the capacitor fits within a given space available between two busses and meets the capacitance, impedance, bandwidth, DC voltage requirement, or a combination thereof characteristics discussed herein. The capacitance of each capacitor may be selected based upon a desired impedance. The capacitance of each capacitor may be selected based upon the frequency range of the signal stimulus. The capacitor may have a capacitance of about 1 pF or larger, about 10 pF or larger, about 100 pF or larger, about 1 nF or larger, or about 10 nF or larger. The capacitor may have a capacitance of about 10 µF or less, preferably about 1 µF or less, more preferably about 100 nF or less, or even more preferably about 50 nF or less. The capacitor may have a capacitance of from about 10 pF to about 1 µF, preferably from about 500 pF to about 500 nF, or more preferably from about 1 nF to about 100 nF. The capacitance of the capacitors may be varied based upon the frequency and impedance of the system, the signal stimulus, or both.

The capacitors include an impedance and the impedance may be selected so that a direct current signal is prevented from passing, and so that an alternating current signal, the alternating voltage signal, or both passes through the solar array. Preferably, the impedance of the one or more capacitors is selected so that a signal generated by a signal stimulus passes through the capacitors so that the signal may be detected by a signal detector, and signals produced by surrounding light are blocked and/or prevented from passing. The impedance of the one or more capacitors may be selected so that the alternating current signal, the alternating voltage signal, or both passes through about one row or more, about two rows or more, or the entire solar array before the impedance becomes too large, the bandwidth becomes too narrow, or both to determine the status of the signal. The impedance may be selected so that the signal produced by the signal stimulus is within a frequency range where the signal passes through the capacitor and a direct current signal is prevented from passing the capacitor. The impedance of the one or more capacitors may be about 10 Ohms or more, about 100 ohms or more, or about 1000 ohms or more. The impedance of the one or more capacitors may be about 100,000 ohms or less, about 50,000 or less, about 25,000 ohms or less, or about 10,000 ohms or less (i.e., each capacitor has an impedance of about 1600 ohms). Preferably, impedance of each capacitor is selected so that a signal with a sufficient amount of bandwidth passes through the solar array so that each connection may be tested. Preferably, the impedance is selected so that bandwidth of the signals unaffected by the increased impedance of the system. The impedance may be selected so that the impedance is larger than the impedance of a solar module. The impedance of a capacitor may be about 10 times or larger, about 25 time or larger, about 50 times or larger, or preferably about 75 times or larger than the impedance of one solar module. The impedance of a capacitor may be about 500 times or less, about 250 times or less, or about 125 times or less the impedance of a solar module (i.e., about 100 times larger than one solar module).

Impedance and bandwidth are inversely proportional. For example, as impedance of the system increases bandwidth through the system decreases and the amount of signal available decreases with the bandwidth. The impedance of the one or more capacitors may be selected so that the overall impedance of the system does not reduce the bandwidth outside of a predetermined bandwidth. The impedance of the one or more capacitors may be selected based upon a total capacitance for a solar array. Impedance may be selected so that bandwidth may be maintained substantially constant from solar module to solar module. Bandwidth may be selected so that the difference change in bandwidth from solar module to solar module is substantially linear.

The impedance of the one or more capacitors may be selected to correspond with a frequency of the detection device so that the signal stimulus may have sufficient bandwidth along the length of the solar array so that the signal may be detected by a signal detector to test the connections. The signal stimulus may be any stimulus that produces a signal through the solar array. The signal stimulus may be any stimulus that produces a signal within a solar array and is free of direct electrical connection with the solar array. The signal stimulus may be any stimulus that produces a signal having a sinusoidal voltage waveform with a frequency that is transmitted through the solar array. Preferably, the signal stimulus may provide a square voltage waveform that is transmitted through the solar array. The signal stimulus may be any stimulus that may be tuned. For example, the frequency of the signal may be varied, adjusted, or both. Preferably, the signal stimulus is one or more lights that flash simultaneously, which are located proximate to and detected by one or more solar modules so that a signal with a square voltage waveform, a sine wave, a quasi-sine wave, or a combination thereof is generated through the solar array. For example, the lights flash on and off causing a square waveform, but the properties of the solar modules, the band pass fitter, of both may cause corners of the square wave to be rounded so that a quasi-sine wave may pass through the solar array and/or detector device. More preferably, the signal stimulus is one or more lights (e.g., strobe light) placed over at least one solar module that flashes at a frequency that may be measured by a signal detector. The signal stimulus may have a sufficient amount of lights and/or power so that the solar module detects the light and produces a signal that is detectable by a signal detector.

The signal stimulus may have a sufficient amount of lights so that the lights produce enough power, current, or both that a signal is induced in the solar array. The signal stimulus preferably, includes a plurality of lights coupled together so that the lights act as one larger light source. Preferably, the signal stimulus produces a sufficient amount of light so that the signal induced through the solar array passes through the one or more capacitors in the solar array so that the signal may be detected. The one or more lights may produce about 100 W/m$^2$ or more, about 200 W/m$^2$ or more, preferably about 300 W/m$^2$ or more, more preferably about 400 W/m$^2$ or more, or more preferably about 500 W/m$^2$ or more of light. The one or more lights may produce about 2,000 W/m$^2$ or less, about 1,500 W/m$^2$ or less, or about 1,000 W/m$^2$ or less of light. The one or more lights may be located in a housing. The housing may be any component that blocks ambient light sources from reaching the solar module. The housing may be any component that may be placed over a solar module so that all other light sources are blocked and the only light source detected by the at least one solar module is the signal stimulus. The housing may block the other light sources so that the frequency of the signal stimulus is clearly introduced to the solar array.

The frequency may be any frequency that may be detected by the detector so that a discontinuity, a partial discontinuity, or continuity may be determined at any location along the solar array being tested. The frequency may be any frequency so that an alternating signal may be induced through the solar module. The frequency may be any frequency greater than 0 Hz (i.e., the signal includes some frequency so that the high impedance of the capacitors do not prevent the signal from passing). The frequency may be adjusted by changing the rate at which the light flashes. The frequency, bandwidth, or both may be adjusted so that the signal strength may be increased and the signal detector may provide a more accurate reading, the capacitors may filter the "noise" out so that the signal detector detects the signal, or both. For example, the signal stimulus may provide a signal with a frequency to one or more solar modules and one or more adjacent solar modules may receive light that may introduce a second signal with a second frequency into the solar array, and the signal detector, the capacitors, or both may filter out the second signal and/or the signal detector may be tuned to only recognize a signal within the first signal's frequency. In another example, surrounding electrical devices may produce a frequency that may be detected by the signal detector and the signal, the signal detector, or both may be tuned to avoid those frequencies (e.g., about 60 Hz and about 120 Hz) and/or not measure these frequencies. The frequency may be any frequency that is detectable by the signal detector, passes through the one or more capacitors, or both. The frequency may be any frequency that is different from the frequency of the surrounding light sources (e.g., any light source that may be used to create power such as electric lighting). The signal stimulus may produce a signal with a frequency of greater than about 0 Hz, about 1 Hz or more, preferably about 10 Hz or more, or more preferably about 100 Hz or more. The signal stimulus may produce a signal with a frequency of about 50,000 Hz or less, preferably about 10,000 Hz or less, most preferably about 5,000 Hz or less. The signal stimulus may produce a signal with a frequency in a range of greater than about 0 Hz to about 50,000 Hz, preferably from about 10,000 Hz to about 1 Hz, more preferably from about 5,000 Hz to about 10 Hz (i.e., about 1,000 Hz or less, but greater than 100 Hz). The signal stimulus may be tuned so that the frequencies selected correspond to a bandwidth that may be passed through the solar array, that may be minimally narrowed by the impedance of the capacitors and/or the system, or both so that a signal may be detected along the length of the solar array and any derogation of the signal strength is minimized.

The bandwidth may be any range of frequencies so that the bandwidth may be detected by the signal detector. The bandwidth as discussed herein is a pass band indicating the frequency of the signal that may pass through the solar array. The bandwidth may be varied. The bandwidth is a range of frequencies where the signal may be detected by a signal detector. Preferably, the bandwidth is substantially similar to the frequencies recited herein. The bandwidth may be greater than about 0 Hz, about 0.1 Hz or more, preferably about 1 Hz or more, or more preferably about 10 Hz or more. The bandwidth may be about 50,000 Hz or less, preferably about 10,000 Hz or less, most preferably about 5,000 Hz or less. The bandwidth may be in a range of 50,000 Hz to about 0 Hz, preferably from about 10,000 Hz to about 1 Hz, more preferably from about 5,000 Hz to about 10 Hz (i.e., about 1,000 Hz or less, but greater than 100 Hz). The signal has an amplitude within the bandwidth and/or frequency.

The amplitude may be at its largest when the amplitude is within the bandwidth. The amplitude may decrease as the frequency becomes further and further from the bandwidth discussed herein. For example, if amplitude is largest within a bandwidth range from about 0.1 Hz to 4,000 Hz and the frequency of the signal is about 8,000 Hz the amplitude may be a factor of two times or more smaller as compared to the amplitude within the bandwidth. The amplitude may be substantially constant when the frequency is within the bandwidth discussed herein. The amplitude of the signal may be about 1.0 db or more, preferably about 2.0 db or more, or more preferably about 2.5 db or more. The amplitude may be about 10 db or less, preferably about 8.0 db or less, or more preferably about 5.0 db or less (i.e., about 3.0 db). Most preferably, the frequency and the bandwidth of one or more solar modules in a solar array may be selected so the amplitude of the signal is large and the signal may be measured using the method taught herein, and a signal detector taught herein may be used to detect the signal generated so that discontinuities and partial discontinuities in the solar array are detected. The amplitude may be increased and/or decreased by adjusting gain of the signal detector.

The signal stimulus may be tuned using one or more of the steps herein so that the signal stimulus provides a signal within a detectable range of the solar module so that a signal in the form of a square voltage waveform passes through the solar module. The frequency response of one or more solar modules in a solar array, one or more comparable solar modules, or both may be measured. Preferably, the frequency response of a comparable solar module may be determined so that the frequency response is determined in the laboratory as opposed to the field. A comparable solar module may be a solar module made of the same materials as the solar modules in the solar array, a solar module from the same manufacturer, or both. The frequency response of a solar module, a row, a solar array, or a combination thereof may be measured so that a signal stimulus may be tuned and a frequency, bandwidth, amplitude, or a combination thereof of a sinusoidal voltage waveform, a square voltage waveform, or both may be transmitted along and/or through a solar module, row, solar array, or a combination thereof. A solar module, a row, a solar array, or a combination thereof may be connected to a function generator, a resistor, an oscilloscope, or a combination thereof so that the frequency response of the solar module, a row, the solar array, or a combination thereof may be determined.

The function generator may provide a waveform to the solar module, row, solar array, or a combination thereof that may pass through the solar module, row, solar array, or a combination thereof and be received by an oscilloscope. The waveform produced by the function generator may have different alternating forms. Preferably, the waveform produced by the function generator is a constant sinusoidal voltage waveform or an alternating square waveform that may be similar in frequency, amplitude, or a combination thereof to a voltage signal produced by the signal stimulus. The function generator may vary the bandwidth, frequency, type, or a combination thereof of the waveform being applied to the solar module, row, solar array, or a combination thereof. The peak to peak output of the function generator may be varied during the tuning step. The peak to peak output may be about 0.1 V or more, about 0.3 V or more, or about 0.5 V or more. The peak to peak output may be about 2.0 V or less, about 1.5 V or less, or about 1.0 V or less (i.e., about 0.8V). The frequency of the waveform may be varied so that the detectable range passing through the solar module, row, solar array, or a combination thereof may be determined.

The frequency of the waveform passed through the solar module, row, solar array, or a combination thereof may be any frequency that may be detected by a signal detector, an oscilloscope, or both. The waveform may have any frequency and/or bandwidth discussed herein for the signal stimulus. Thus, the frequency and/or bandwidth determined in the step of determining the frequency response of a solar module, a row, a solar array, or a combination thereof may be used to tune the signal stimulus so that the signal is detectable by the detector device. The frequency, bandwidth, or both may be monitored using any device that may measure frequency, bandwidth, or both (e.g., an oscilloscope). The bandwidth may be monitored so that a bandwidth may be selected where the amplitude is at its maximum. A bandwidth may be selected where the amplitude is large, is within a detectable range of the signal detector, or both. The waveform from the function generator may pass through one or more resistors before entering the solar module, the row, the solar array, or a combination thereof.

The resistor preferably is located between the function generator and a solar module. The resistor may be any size resistor. The resistor may stabilize the signal from the function generator so that the oscilloscope may detect the waveform being produced. The resistor may stabilize the amplitude output of the function generator within a frequency range so that the bandwidth, frequency, amplitude or a combination thereof of the waveform outputted by the solar module remains substantially constant. The resistor may be sufficiently sized so that the resistor provides a divider in the circuit so that changing impedance of the module may be measured as the frequency is changed, a minimal load is provided on the function generator in addition to the impedance of the solar module, the function generator may output a constant amplitude over a frequency range so that a load will not drop below an output impedance of the function generator, or a combination thereof. The resistor may be substantially equal to the voltage output of the function generator. The resistor may be about 10Ω or more, about 20Ω or more, about 30Ω or more, or about 40Ω or more. The resistor may be about 100Ω or less, about 90Ω or less, about 80Ω or less, about 70Ω or less, or about 60Ω or less (i.e., about 49Ω).

After the frequency range, bandwidth, or both of the one or more solar modules is determined the signal stimulus, the signal detector, or both are tuned so that the signal stimulus outputs a signal within the frequency range, the bandwidth, or both and the signal detector monitors the frequency range, bandwidth, or both being emitted by the signal stimulus and amplitude of the signal is monitored. For example, the speed that the lights of the signal stimulus turning off and on may be adjusted so that a signal outputted by the solar module has a square voltage waveform with a frequency, bandwidth, amplitude or a combination thereof within the determined ranges.

The signal created may be any signal that may be detected by a signal detector discussed herein. The signal detector may be any device that may detect an alternating current signal, an alternating voltage signal, or both. The signal detector may detect a waveform. The signal detector may detect a current level, a voltage level, or both to determine the status of a connection. The signal detector may be used to detect a signal or the lack of a signal to determine a status. The signal detector may detect the presence of an induced signal. The signal detector may measure a signal having an alternating voltage of about 10 V or less, about 8 V or less, or about 6 V or less. The signal detector may measure a signal having an alternating voltage of about 1 mV or more, about 5 mV or more, or about 10 mV or more. The signal detector may detect the presence of an alternating voltage from about 10 V to about 1 mV, preferably from 8 V to about 3 mV, or more preferably from about 6 V to about 5 mV. The signal detector may convert a voltage to a signal strength to determine the status of a location. The signal detector may include a processor, a microprocessor, a microcontroller, or a combination thereof that compares a measured signal strength to a calculated signal strength. The signal detector may include a wireless transmitter.

The wireless transmitter may be any transmitter that may alert the user that the connection being tested is continuous, discontinuous, or both. The wireless transmitter may transmit data, results, or both. The wireless transmitter may transmit a signal to a display pendant a wireless display pendant, a display on the signal stimulus, or a combination thereof. The signal detector may transmit a signal to the user via a wire or cable so that the user knows the status of the connection. The signal detector may include a speaker that makes one noise when the connection is continuous and a different noise if the connection is discontinuous. The signal detector may be used in a method discussed herein to determine the status of a connection.

The present teachings include a method of testing and/or detecting discontinuities, partial discontinuities, opens, or a combination thereof in the improved solar array discussed herein. The method may include one or more of the steps discussed herein in any order. The method may include a step of inducing a signal through a solar module, a row, the solar array, or a combination thereof. The method may include a step of applying a signal stimulus to one or more solar modules. The signal stimulus may be moved from solar module to solar module. The signal stimulus may be moved from a first end towards a second end of the solar array or vice versa. Preferably, the signal stimulus is moved from a location proximate to an inverter to adjacent solar modules in a direction away from the inverter. The signal stimulus may be moved from row to row. The signal stimulus may invoke an alternating current waveform signal, a sinusoidal alternating voltage waveform signal, or both through a solar module, a row, the solar array, or a combination thereof. The signal stimulus may invoke a square alternating current signal, a square alternating voltage signal, or both through a solar module, a row, the solar array, or a combination thereof. The alternating current waveform signal, the alternating voltage waveform signal, or both may be referred to herein as the signal. The signal may be measured using any detector discussed herein.

The signal detector may be electrically connected to the solar array. The signal detector may be connected to a buss termination point, to the solar array proximate to the inverter, at the end of a row, to an integrated flashing piece, to a solar module, or a combination thereof. Preferably, the signal detector is electrically connected directly to the same row as the signal stimulus. Preferably the inverter is disconnected and the signal detector is electrically connected to the system at the buss termination point, and the signal stimulus is first applied to the solar module closest to the signal detector. The signal detector may be connected to the first buss, the second buss, or both. Preferably, the signal detector is not connected to the signal stimulus. The signal detector monitors the signal induced by the signal stimulus. The signal detector may monitor the level of the current, the level of voltage, the bandwidth, for the presence of a signal, or a combination thereof. Preferably, the signal detector is used to determine if a signal is present and if a signal is present all connections between the signal stimulus and signal detector are continuous (i.e., closed). If the status of the connection is determined to be continuous the signal stimulus is moved to the next solar module where the step of determining and/or testing the status of the signal is repeated. If the status of the next adjoining connection is determined to be continuous then the step of moving and determining is repeated until the discontinuity is discovered. It is contemplated that the signal stimulus may be moved more than one solar module at a time so that fewer steps of determining may be used. For example the signal stimulus may be moved 2, 3, 4, 5, 6, or 7, solar modules at a time and when a discontinuity is located the signal stimulus is moved back towards the signal detector until the discontinuity is pinpointed. The signal stimulus may be moved from row to row. The method of testing the first buss and the second buss may be different and/or the same. The first buss may be tested by moving the signal stimulus from module to module, row to row, or any solar module location therebetween. The second buss may be tested by moving the signal stimulus from row to row. Preferably, both the first buss and the second buss are tested concurrently. The signal strength, the gain of the signal detector, or both may be varied during the step of determining. Once a discontinuity and/or partial discontinuity is located the connector, solar module, integrated flashing piece, wire first buss, second buss, or a combination thereof may be replaced, repaired, or both.

As the distance, the number of solar modules, or both between the signal stimulus and the signal detector increases the signal strength, the bandwidth, the amplitude, or a combination thereof may begin to decrease. If the signal degrades to a point where the signal can no longer be measured, monitored, or both the signal detector may be moved, the gain of the signal detector may be varied, the amount of power emitted by the signal stimulus may be increased, or a combination thereof. For example, the brightness of the lights in the signal detector may be increased, the number of lights turned on may be increased, or both.

FIG. 1 illustrates a solar array 2. The solar array includes a plurality of solar modules 10. Each solar module 10 is connected to an adjacent solar module by a connector 30. A row of solar modules 10 connected together form a row 4. The ends of the rows 4 include an integrated flashing piece 40 that connects the adjoining rows 4 together so that a solar array is formed 2. The first solar module 12 is connected to an inverter (not shown) at a buss termination point 22 so that the power generated by the solar array may be used. The last solar module 14 is connected to a single integrated flashing piece 42 that connects a first buss 16 and a second buss 18 of a solar module together so that power is directed towards the inverter (not shown).

Figure 2:
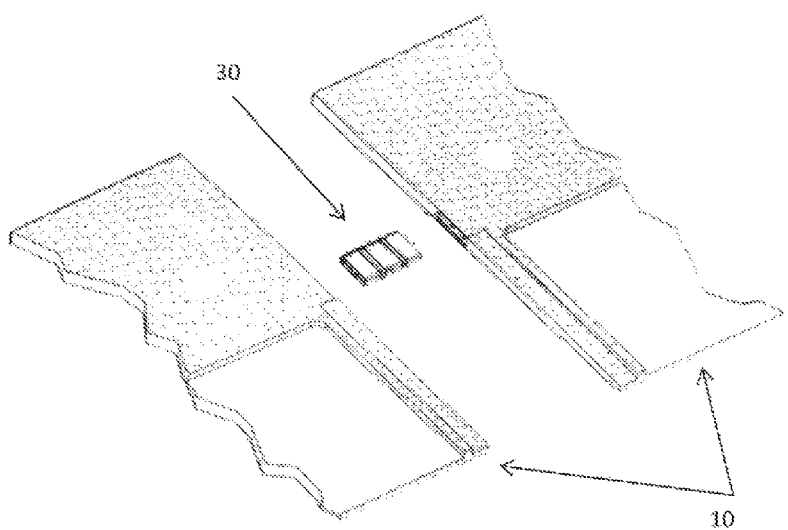
FIG. 2 illustrates one possible electrical connector between two solar modules.
Figure 3:
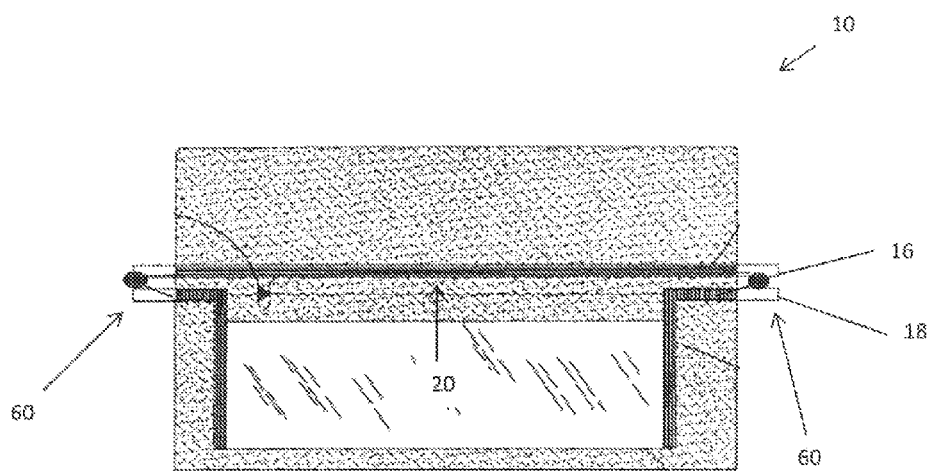
FIG. 3 illustrates one possible buss configuration of a solar module.

FIG. 2 illustrates a close up exploded view of FIG. 1 showing one possible connector 30 that may be used to connect to solar modules 10. FIG. 3 illustrates a solar module 10 having a first buss 16 and a second buss 18. The first buss bar 16 and the second buss bar 18 include capacitors 60 on both sides of the solar module 10. The first buss 16 passes directly through the solar module 10 and the second buss 18 extends along the body portion so that power can be passed through a connector (not shown).

Figures 4A, 4B:
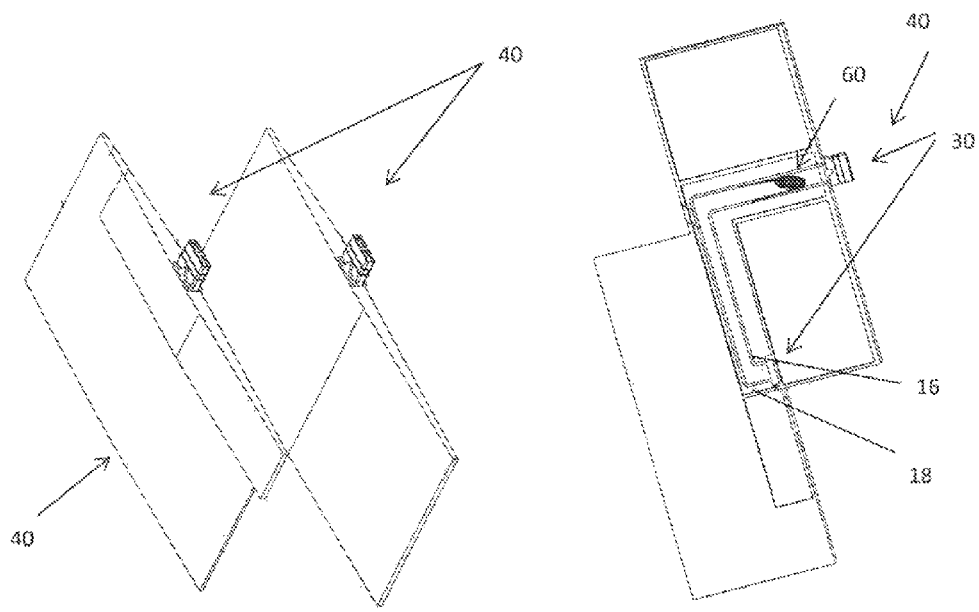
FIG. 4A illustrates one possible integrated flashing piece and FIG. 4B illustrates the internal components of an integrated flashing piece.

FIGS. 4A and 4B are close-up views of the intergraded flashing piece 40 of FIG. 1. FIG. 4A illustrates an integrated flashing piece 40. The integrated flashing piece 40 connects two adjacent rows 4 (not shown) so that power flows from one row to another row and to the inverter (not shown). FIG. 4B illustrates one possible internal configuration of an integrated flashing piece 40. The integrated flashing piece includes a connector 30 for connecting the integrated flashing piece 40 to a solar module 10 (not shown). The integrated flashing piece 40 includes a first buss 16 and a second buss 18, and the first buss 16 and the second buss 18 are connected via a capacitor 60.

Figure 5:
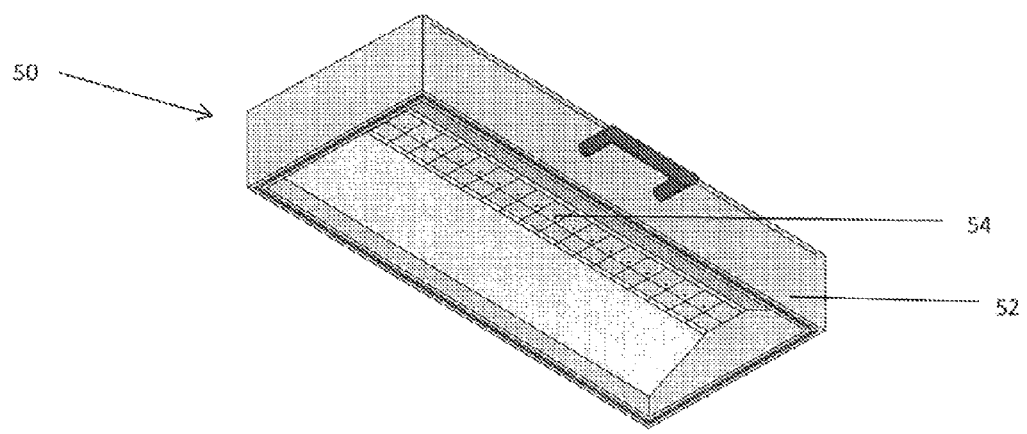
FIG. 5 illustrates one possible configuration for a signal stimulus and housing.

FIG. 5 illustrates one possible signal stimulus 50. The signal stimulus has a housing 52 and lights 54. During use the signal stimulus 50 covers a solar module 10 (not shown) and the lights 54 flash so that a signal is induced through the solar module 10 (not shown) and the solar array (not shown).

Figure 6:
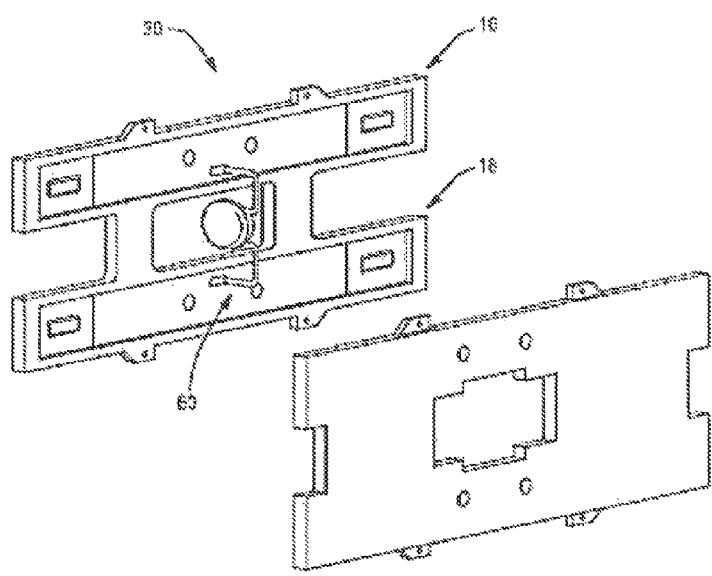
FIG. 6 illustrates one example of a connector including a capacitor.

FIG. 6 illustrates a connector 30 opened so that the first buss 16 and the second buss 18 are shown. The first buss 16 and the second buss 18 are connected via a capacitor 60 spanning therebetween.

Figure 7:
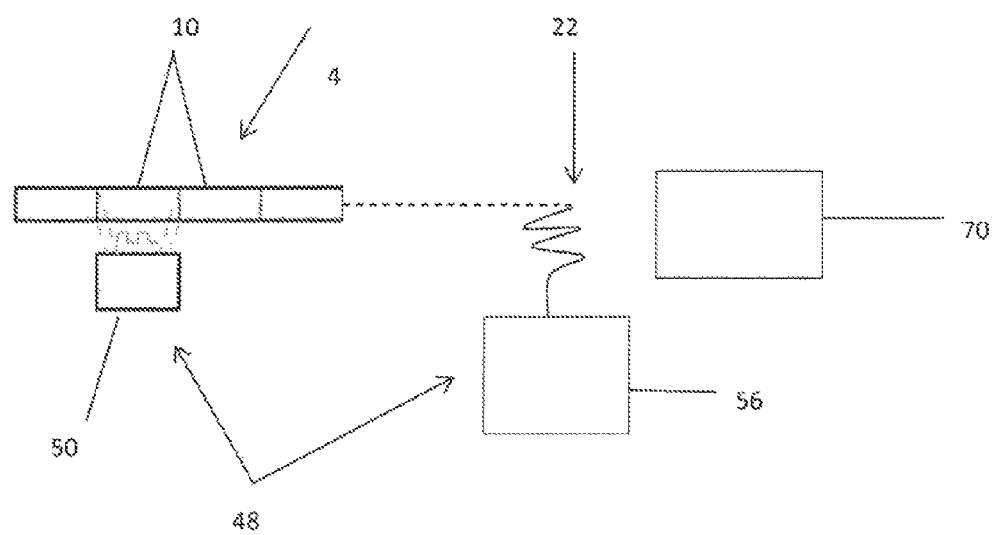
FIG. 7 illustrates a detecting device being used to test connections.

FIG. 7 illustrates a detection device 48 located proximate to a row 4 of solar modules 10 so that connections of the row 4 are tested. The inverter 70 is disconnected from the buss termination point 22 and the signal detector 56 is connected to the solar array at the buss termination point 22. A signal stimulus 50 is located over one solar module 10 to induce a signal. The signal stimulus 50 is moved to adjacent solar modules 10 until a discontinuity is detected.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

We claim:

1. A kit comprising one or more of the following:
   one or more solar modules;
   one or more connectors; and
   one or more integrated flashing pieces that connect two adjacent rows of the one or more solar modules together or a row of the one or more solar modules to an inverter;
   wherein the one or more solar modules, the one or more connectors, and the one or more integrated flashing pieces are operably coupled to a first buss and a second buss;
   wherein a capacitor is located within the one or more solar modules, the one or more connectors, the one or more integrated flashing pieces, or a combination thereof and the capacitor extends between the first buss and the second buss so that the capacitor blocks direct current from passing between the first buss and the second buss and allows an alternating current signal, an alternating voltage signal, or both to pass between the first buss and the second buss so that a discontinuity, partial discontinuity, or continuity of the one or more solar modules, the one or more connectors, the one or more integrated flashing pieces, or a combination of connections therebetween are detectable when the one or more solar modules, the one or more connectors, and the one or more integrated flashing pieces are electrically connected.

2. The kit of claim 1, wherein the capacitor has a capacitance of 1.0 mF or less.

3. The kit of claim 1, wherein the capacitor has a capacitance from about 1 nF to about 100 nF.

4. The kit of claim 1, wherein the capacitor has an impedance of about 25,000 Ohms or less.

5. A solar array comprising:
   a plurality of solar modules connected together forming rows of solar modules;
   one or more integrated flashing pieces connecting one of the rows of solar modules to an inverter, two of the rows of solar modules together, or both;
   one or more connectors located between and electrically connecting the plurality of solar modules together, or located between a row of the solar modules and the one or more integrated flashing pieces; and one or more capacitors electrically connected to and located within one or more of the plurality of solar modules, the one or more connectors, the one or more integrated flashing pieces, or a combination thereof;

wherein the one or more solar modules, the one or more connectors, and the one or more integrated flashing pieces have a first buss and a second buss and the one or more capacitors are connected to the first buss and the second buss; and wherein the one or more capacitors block direct current from passing between the first buss and the second buss so that a discontinuity, partial discontinuity, or both along the solar array are detected by measuring an alternating current signal, an alternating voltage signal, or both as a signal stimulus is moved along the solar array.

6. The solar array of claim 5, where the one or more capacitors are located in the plurality of solar modules, the one or more connectors, the one or more integrated flashing pieces, or a combination thereof.

7. The solar array of claim 5, wherein the one or more capacitors each have a capacitance of 1.0 mF or less.

8. The solar array of claim 5, wherein the one or more capacitors each have a capacitance from about 1 nF to about 100 nF.

9. The solar array of claim 5, wherein the one or more capacitors each have an impedance of about 25,000 Ohms or less.

10. The solar array of claim 5, wherein the measured alternating current signal, the alternating voltage signal, or both have a frequency of about 1000 Hz or less, but greater than about 0 Hz.

11. A method comprising:
inducing a signal by applying the signal stimulus to one or more of the solar modules of the solar array of claim 5 so that the signal stimulus produces an alternating current signal and an alternating voltage signal;
measuring the alternating voltage signal, the alternating current signal, or both at one or more points along the solar array using a detector; and
providing feedback regarding whether the solar array has continuity, discontinuity, or a partial discontinuity based upon a measurement taken at the one or more points along the solar array.

12. The method of claim 11, wherein the method includes the step of moving the signal stimulus which is a strobe light to a different solar module so that a subsequent measurement is taken.

13. The method of claim 11, wherein the method includes the step of moving the strobe light further from the detector and taking a subsequent measurement.

14. The method of claim 11, wherein the method includes a step of electrically connecting the detector to the solar array.

15. The method of claim 14, wherein the detector is connected to the first buss, the second buss, or both at a buss termination point at an inverter.

16. The method of claim 11, wherein the method includes a step of varying one or more characteristics of the signal stimulus based on the number of solar modules positioned between the detector and the signal stimulus.

17. The method of claim 16, wherein the method includes a step of comparing a measurement taken at the one or more points along the solar array to a calculated alternating current signal, a calculated alternating voltage signal, or both, and determining whether the solar array has continuity, discontinuity, or a partial discontinuity.

18. The method of claim 11, wherein the method includes a step of determining a frequency response of one or more of the solar modules and tuning the signal stimulus so that a frequency of the signal stimulus correlates to the frequency of the one or more solar modules.

19. The method of claim 14, wherein the method includes disconnecting the inverter from the solar array, and electrically connecting the detector to the solar array.

20. The kit of claim 1, wherein each of the one or more solar modules, the one or more connectors, and the one or more integrated flashing pieces each include a capacitor.

* * * * *